(12) United States Patent
Crawford

(10) Patent No.: US 7,201,740 B2
(45) Date of Patent: Apr. 10, 2007

(54) FORWARD-SHIELDING BLOOD COLLECTION SET

(75) Inventor: Jamieson Crawford, New York City, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/882,659

(22) Filed: Jul. 1, 2004

(65) Prior Publication Data

US 2006/0079847 A1    Apr. 13, 2006

(51) Int. Cl.
*A61M 5/32* (2006.01)
(52) U.S. Cl. .................. 604/198; 604/110; 604/263
(58) Field of Classification Search ............... 604/110, 604/177, 116, 198, 263
See application file for complete search history.

(56) References Cited

U.S. PATENT DOCUMENTS

| | | | |
|---|---|---|---|
| 5,085,639 A | 2/1992 | Ryan | |
| 5,088,982 A | 2/1992 | Ryan | |
| 5,112,311 A | 5/1992 | Utterberg et al. | |
| 5,120,320 A | 6/1992 | Fayngold | |
| 5,154,699 A | 10/1992 | Ryan | |
| 5,176,655 A | 1/1993 | McCormick et al. | |
| 5,186,712 A * | 2/1993 | Kelso et al. ............ | 604/165.03 |
| 5,192,275 A * | 3/1993 | Burns ......................... | 604/263 |
| 5,266,072 A | 11/1993 | Utterberg et al. | |
| 5,290,264 A | 3/1994 | Utterberg et al. | |
| 5,300,039 A * | 4/1994 | Poulsen ...................... | 604/198 |
| 5,562,636 A | 10/1996 | Utterberg et al. | |
| 5,562,637 A | 10/1996 | Utterberg et al. | |
| 5,746,726 A * | 5/1998 | Sweeney et al. ............ | 604/263 |
| 5,779,679 A * | 7/1998 | Shaw ........................ | 604/158 |
| 5,951,525 A | 9/1999 | Thorne et al. | |
| RE36,398 E | 11/1999 | Byrne et al. | |
| RE36,447 E | 12/1999 | Byrne et al. | |
| 6,537,259 B1 * | 3/2003 | Niermann ................... | 604/263 |
| 6,659,983 B2 * | 12/2003 | Crawford et al. ........... | 604/192 |
| 2003/0078540 A1 | 4/2003 | Saulenas et al. | |
| 2003/0135157 A1 | 7/2003 | Saulenas et al. | |
| 2003/0144632 A1* | 7/2003 | Hommann et al. ......... | 604/198 |
| 2003/0181869 A1 | 9/2003 | Swensen et al. | |
| 2003/0181871 A1 | 9/2003 | Wilkinson et al. | |
| 2004/0010227 A1* | 1/2004 | Riesenberger et al. ...... | 604/110 |
| 2005/0119627 A1* | 6/2005 | Crawford ..................... | 604/263 |

* cited by examiner

*Primary Examiner*—Kevin C. Sirmons
*Assistant Examiner*—Andrew Gilbert
(74) *Attorney, Agent, or Firm*—Mark Lindsey

(57) ABSTRACT

A blood collection set includes a needle having a puncture tip, a hub supporting the needle and including a release member, a safety shield, a drive member, and a packaging shield disposed on the hub. The safety shield is movable from a retracted position within the hub to an extended position shielding the puncture tip of the needle. The packaging shield encloses the puncture tip of the needle in the retracted position of the safety shield. The shielding feature of the blood collection set is activated by applying radial pressure to the release member, causing the release member to release the packaging shield from the hub, and maintain the safety shield in the retracted position. Upon sufficient or partial release of radial pressure, the drive member disengages the release member from the safety shield and moves the safety shield from the retracted position to the extended positions.

32 Claims, 7 Drawing Sheets

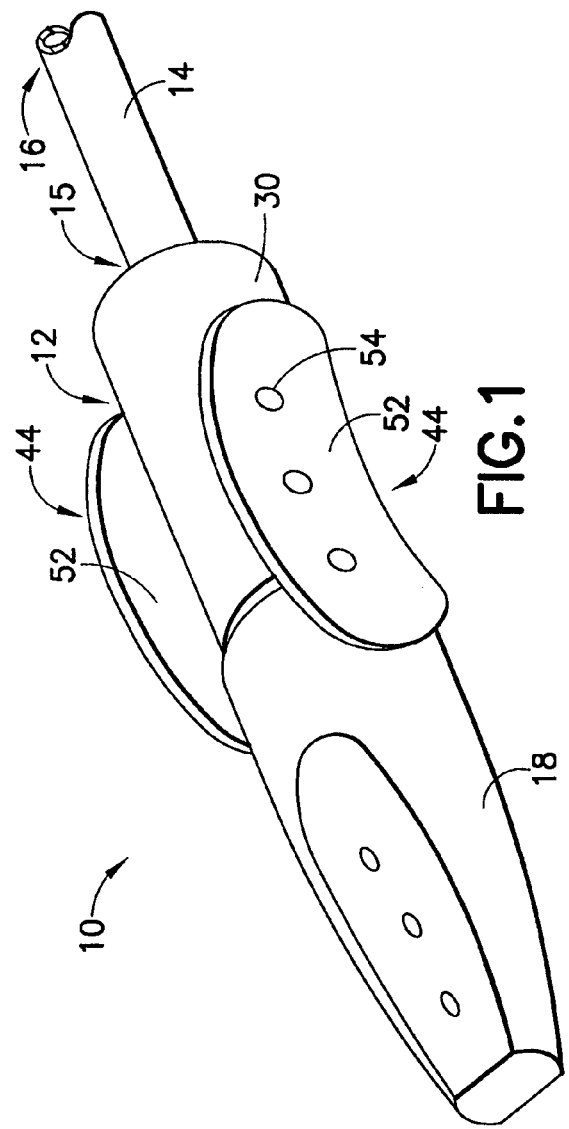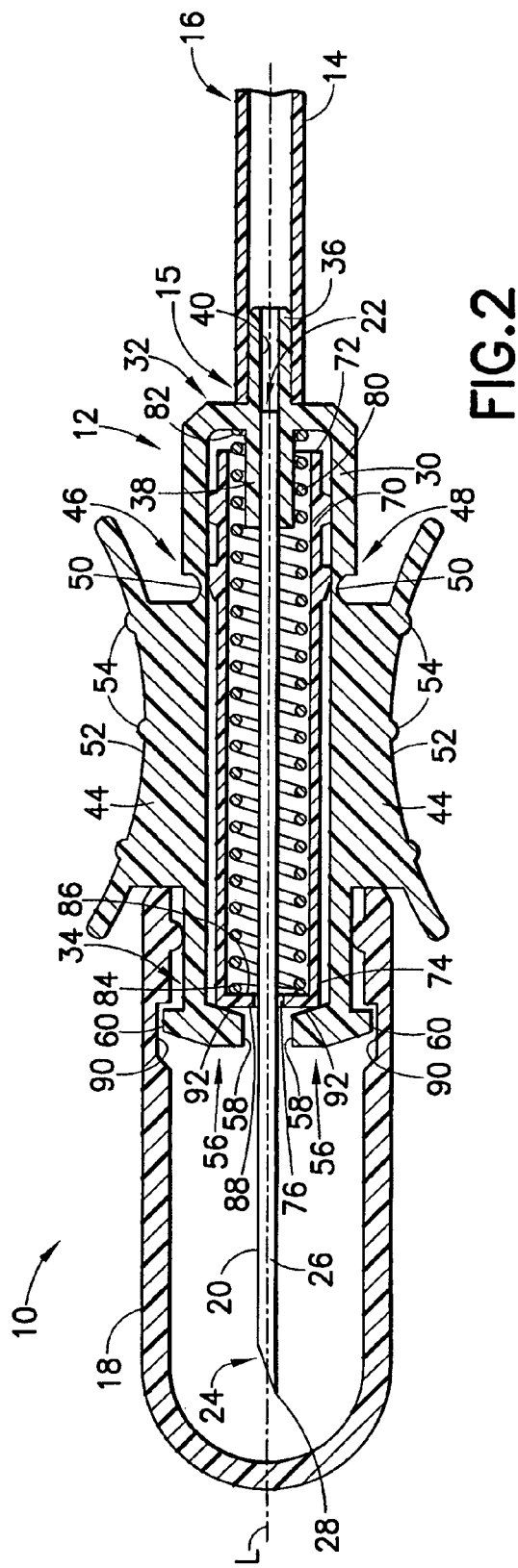

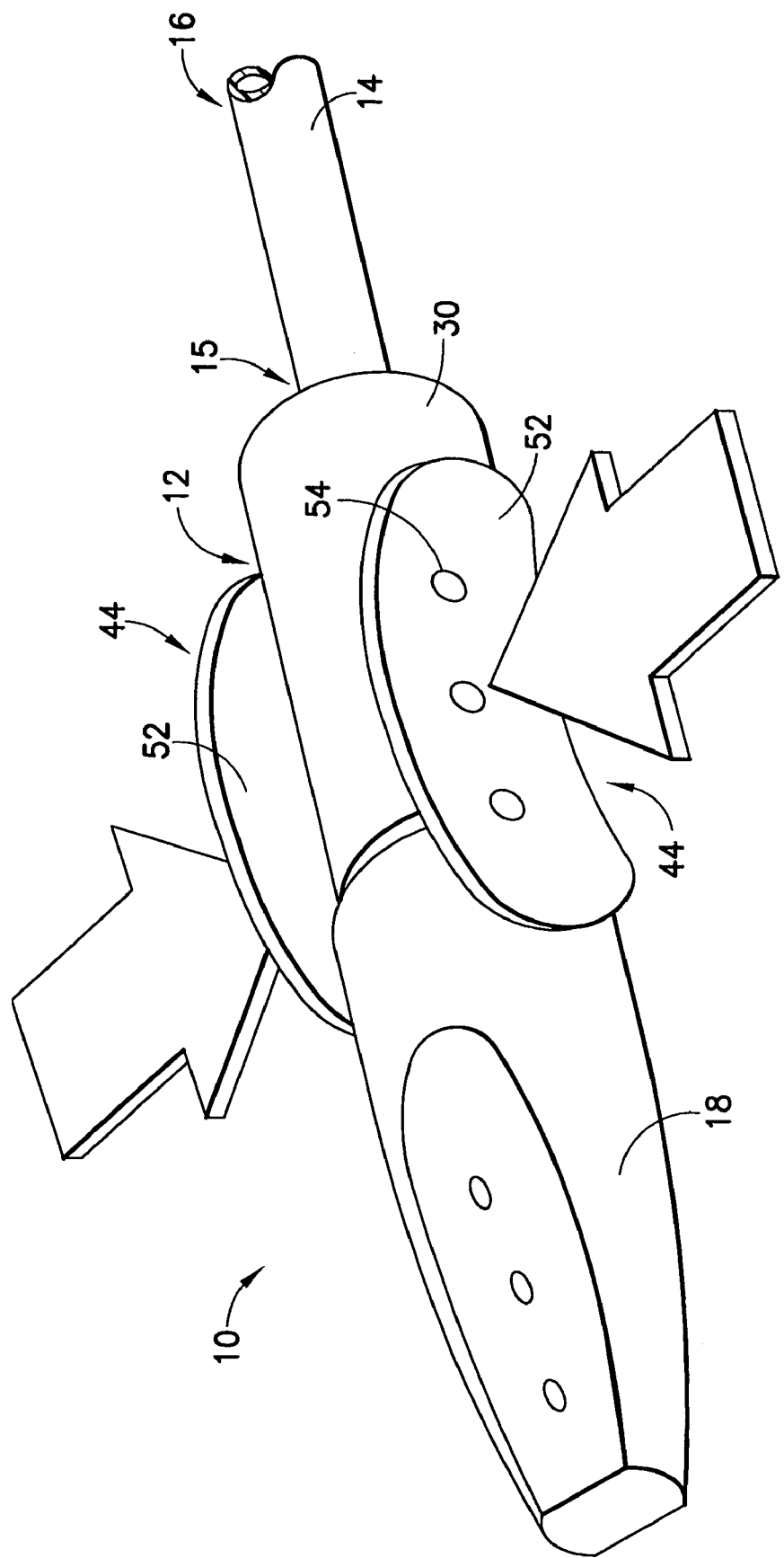

FORWARD-SHIELDING BLOOD COLLECTION SET

BACKGROUND OF THE INVENTION

1. Field of the Invention

The present invention relates to blood collection sets for safe and convenient handling of needles used in blood collection procedures. More particularly, the present invention relates to a blood collection set including a forward-shielding needle safety shield for protecting users from a used needle tip, and further including a packaging shield adapted to prevent premature actuation of the safety features of the blood collection set.

2. Description of Related Art

Disposable medical devices having medical needles are used for administering medication or withdrawing fluid from the body of a patient. Such disposable medical devices typically include blood collecting needles, fluid handling needles, and assemblies thereof. Current medical practice requires that fluid containers and needle assemblies used in such devices be inexpensive and readily disposable. Consequently, existing blood collection devices often employ some form of durable, reusable holder on which detachable and disposable medical needles and fluid collection tubes may be mounted. A blood collection device of this nature may be assembled prior to use and then disassembled after use. Thus, these blood collection devices allow repeated use of a relatively expensive holder upon replacement of relatively inexpensive medical needles and/or fluid collection tubes. In addition to reducing the cost of collecting blood specimens, these blood collection devices help minimize the production of hazardous waste material.

A blood collection device or intravenous (IV) infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin, flexible thermoplastic tube is connected to the hub and communicates with the lumen of the needle cannula. The end of the plastic tube remote from the needle cannula may include a fixture for connecting the needle cannula to a holder or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies often employ a safety shield that can be moved into shielding engagement with a used needle cannula to minimize risk of an accidental needle stick.

Some needle safety shields are referred to as "tip guards" and include a small rigid guard that may be telescoped along the length of the needle cannula and extended over the pointed distal end of the needle cannula for protection. Such conventional tip guards may include some form of tether for limiting the travel of the tip guard to the length of the needle cannula. An example of the foregoing is disclosed by U.S. Pat. No. 5,176,655 to McCormick et al. The McCormick et al. patent discloses the use of flexible loop-like straps for limiting the distal movement of a tip guard.

Needle shields that incorporate movable tip guards are typically manually actuated. For example, U.S. Pat. Nos. Re. 36,447 and Re. 36,398, both to Byrne et al., disclose a safety device for a hypodermic needle that includes a plastic sheath, which is used to cover the puncture tip of the needle. The plastic sheath incorporates a thumb guard, which the user of the safety device may grasp to move the plastic sheath to a position covering the puncture tip of the needle. U.S. Pat. No. 5,951,525 to Thorne et al. discloses a manually operated safety needle apparatus that includes two pairs of opposed legs adapted to move the tip guard of the apparatus to a position covering the used needle cannula. U.S. Pat. Nos. 5,562,637 and 5,562,636, both to Utterburg, disclose a rectangular needle protector sheath for use with a needle cannula that may be extended over the needle cannula after it is used. Other prior art devices, such as those disclosed by U.S. Pat. No. 5,290,264 to Utterberg and U.S. Pat. No. 5,192,275 to Burns, provide "grippable" members attached to the tip guards to facilitate moving the tip guards to a position covering the puncture tip of a needle cannula. In addition to providing gripping members for moving the tip guards, prior art devices in this area often include flexible wings, which are used as means for securing the needle assemblies to the body of a patient during a medical procedure. Examples of "winged" needle assemblies may be found in U.S. Pat. No. 5,120,320 to Fayngold; and U.S. Pat. Nos. 5,154,699; 5,088,982; and 5,085,639 all to Ryan. Other prior art in this area includes U.S. Pat. Nos. 5,266,072 and 5,112,311, both to Utterberg et al., which also disclose guarded winged needle assemblies.

Conventional tip guards, such as those discussed hereinabove, often include a structure that lockingly engages over the pointed distal end of the used needle cannula to prevent a re-exposure of the needle cannula. The structure for preventing the re-exposure of the needle cannula may include a metallic spring clip or a transverse wall formed integrally with one end of the tip guard. An example of a metallic spring clip is disclosed by the McCormick et al. patent discussed previously.

Conventional tip guards, such as those discussed hereinabove, often further require extensive mechanics for positioning the tip guard over the needle cannula. This results in complex arrangements that are costly to manufacture and assemble. Additionally, operation of the needle assemblies to move the tip guard into the proper position over the pointed distal end of the needle cannula requires substantial manual manipulation by the user of the device, exposing the user to potential needle-stick wounds.

In view of the foregoing, a need exists for a blood collection set including a shielding needle assembly that achieves secure and effective shielding of a used needle cannula, and which is simple and inexpensive to manufacture and easy to operate. An additional need exists for a blood collection set that is passively operated and includes structures that prevent premature actuation of the safety features of the blood collection set.

SUMMARY OF THE INVENTION

The foregoing needs are fulfilled with a shielding blood collection set and a shielding needle assembly in accordance with the present invention. The shielding blood collection set generally includes a flexible tube, a needle cannula, a hub, a safety shield, and a drive member. The flexible tube has opposed first and second ends, with the first end of the tube adapted for connection to a fixture such as a receptacle or holder. The needle cannula has a proximal end and a distal end with a puncture tip. The hub has a proximal end and a distal end. An interior portion of the hub proximal end supports the needle cannula proximal end, and the second end of the tube is connected to an exterior portion of the hub proximal end. The hub further includes at least one release member. The safety shield is movably associated with the hub from a retracted position disposed generally coaxially with the hub, to an extended position shielding the puncture tip of the needle cannula. The drive member is associated with the hub and is generally adapted to move the safety shield from the retracted to the extended positions. The hub and at least one release member are generally adapted such that application of radial pressure to the at least one release member causes the at least one release member to engage the safety shield and maintain the safety shield in the retracted position, and at least partial release or lessening of the radial pressure allows the drive member to disengage the at least one release member from the safety shield and move the safety shield from the retracted position to the extended position.

The drive member may be a coil spring. The at least one release member may be pivotally connected to the hub, for example, substantially at the hub proximal end.

A finger tab may be provided on the at least one release member for applying the radial pressure to the at least one release member. The at least one release member may include a pair of opposing release members pivotally connected to the hub, for example, substantially at the hub proximal end. A finger tab may be provided on each of the release members for applying the radial pressure to the release members.

The at least one release member may include a locking tab adapted to engage a locking recess in the safety shield in the extended position of the safety shield. The locking recess may extend circumferentially about the safety shield.

A packaging shield may be disposed on the hub distal end and enclose the puncture tip of the needle cannula in the retracted position of the safety shield. The at least one release member may include a locking tab engaging a locking groove in the packaging shield, generally preventing removal of the packaging shield until the application of the radial pressure on the at least one release member causes the at least one release member to pivot radially inward and disengage the locking tab from the locking groove.

The present invention is further directed to a shielding needle assembly that may be used, for example, in the blood collection set described hereinabove. The shielding needle assembly in one embodiment of the present invention includes a needle cannula, a hub associated with the needle cannula, a safety shield for shielding at least a distal end of the needle cannula, and a drive member for actuating or moving the safety shield. The needle cannula has a proximal end and a distal end with a puncture tip. The hub supports the needle cannula. The hub includes at least one release member. The safety shield is movably associated with the hub from a retracted position disposed generally coaxial with the hub to an extended position shielding the puncture tip of the needle cannula. The drive member is associated with the hub and is generally adapted to move the safety shield from the retracted position to the extended position. The hub and at least one release member may be adapted such that application of radial pressure to the at least one release member causes the at least one release member to engage the safety shield and maintain the safety shield in the retracted position, and at least partial release or lessening of the radial pressure allows the drive member to disengage the at least one release member from the safety shield and move the safety shield from the retracted position to the extended position.

The drive member may be a coil spring. The at least one release member may be pivotally connected to the hub, for example, substantially at the hub proximal end. A finger tab may be provided on the at least one release member for applying the radial pressure to the at least one release member.

The at least one release member may include a pair of opposing release members pivotally connected to the hub, for example, substantially at the hub proximal end. A finger tab may be provided on each of the release members for applying the radial pressure to the release members.

The at least one release member may include a locking tab adapted to engage a locking recess in the safety shield in the extended position of the safety shield. The locking recess may extend circumferentially about the safety shield.

In a modification of the foregoing shielding needle assembly, the shielding needle assembly may further include a packaging shield disposed on a distal end of the hub and enclose the puncture tip of the needle cannula in the retracted position of the safety shield. The at least one release member may include a locking tab engaging a locking groove in the packaging shield to prevent inadvertent removal of the packaging shield. The hub and at least one release member may be further adapted such that application of radial pressure to the at least one release member causes the at least one release member to pivot radially inward and disengage the locking tab from the locking groove, thereby generally releasing the packaging shield from the hub, and further causing the at least one release member to engage the safety shield and maintain the safety shield in the retracted position. At least partial release or lessening of the radial pressure preferably allows the drive member to disengage the at least one release member from the safety shield and move the safety shield from the retracted position to the extended position.

The at least one release member may further include a second locking tab adapted to engage a locking recess in the safety shield in the extended position of the safety shield. The locking recess in the safety shield may extend circumferentially about the safety shield.

In another embodiment, the present invention is a shielding needle assembly with a passively-removable packaging shield. The needle assembly generally includes a needle cannula, a hub, and the passively-removable packaging shield. The needle cannula includes a proximal end and a distal end with a puncture tip. The hub supports the needle cannula. The packaging shield is disposed about a distal end of the hub and encloses the puncture tip of the needle cannula prior to using the needle assembly. The packaging shield is releasably associated with the distal end of the hub. The hub includes at least one release member disposed at least partially within the packaging shield, which is adapted to flex radially inward toward a central longitudinal axis of the needle assembly upon applying radial pressure thereto, to allow substantial automatic release of the packaging shield from the distal end portion of the hub. Thus, application of radial pressure applied to the at least one release member is required for removal of the packaging shield from the hub, and sequential change, for example lessening, is radial pressure applied to the at least one release member is required for allowing the drive member to disengage the at least one release member from the safety shield and move the safety shield from the retracted position to the extend position.

The hub is preferably capable of direct or indirect fluid communication with a syringe through, for example, a syringe's male luer distal taper, or with a blood collection tube receptacle or holder.

The at least one release member may be pivotally connected to the hub, for example, substantially at a proximal end of the hub. The at least one release member may include a pair of opposing release members pivotally connected to the hub, for example, substantially at the proximal end of the hub. A finger tab may be provided on each of the release members for applying the radial pressure to the release members and pivoting the release members radially inward toward the central longitudinal axis of the needle assembly.

The present invention is further directed to a method of actuating a shielding needle assembly, for example, one of the shielding needle assemblies discussed previously. The method generally includes providing the shielding needle assembly including a needle cannula having a puncture tip, a hub supporting the needle cannula, a safety shield movably associated with the hub and disposed generally coaxially with the hub, and a drive member associated with the hub for moving the safety shield relative to the hub, the hub including at least one release member. Additionally, the method includes applying radial pressure to the at least one release member, such that the at least one release member engages the safety shield to maintain the safety shield in a retracted position disposed generally coaxially with the hub. The method may include a further step of at least partially releasing the radial pressure, such that the drive member automatically disengages the at least one release member from the safety shield and moves the safety shield from the retracted position to an extended position shielding the puncture tip of the needle cannula. As indicated previously, the shielding needle assembly may further include a packaging shield disposed on a distal end of the hub and enclosing the puncture tip of the needle cannula in the retracted position of the safety shield. The at least one release member may have a locking tab engaging a locking groove in the packaging shield, which prevents removal of the packaging shield until the application of the radial pressure to the at least one release member causes the at least one release member to displace radially inward into the hub and disengages the locking tab from the locking groove.

Further details and advantages of the present invention will become apparent from the following detailed description when read in conjunction with the accompanying drawings.

BRIEF DESCRIPTION OF THE DRAWINGS

FIG. 1 is a perspective view of a shielding blood collection set in accordance with the present invention and having a releasable packaging shield disposed at a distal end of the blood collection set;

FIG. 2 is a longitudinal cross-sectional view of the blood collection set of FIG. 1;

FIG. 8 is a perspective view showing the direction of forces needed to actuate the shielding needle assembly portion of the blood collection set.

DETAILED DESCRIPTION OF THE INVENTION

Figure 3:
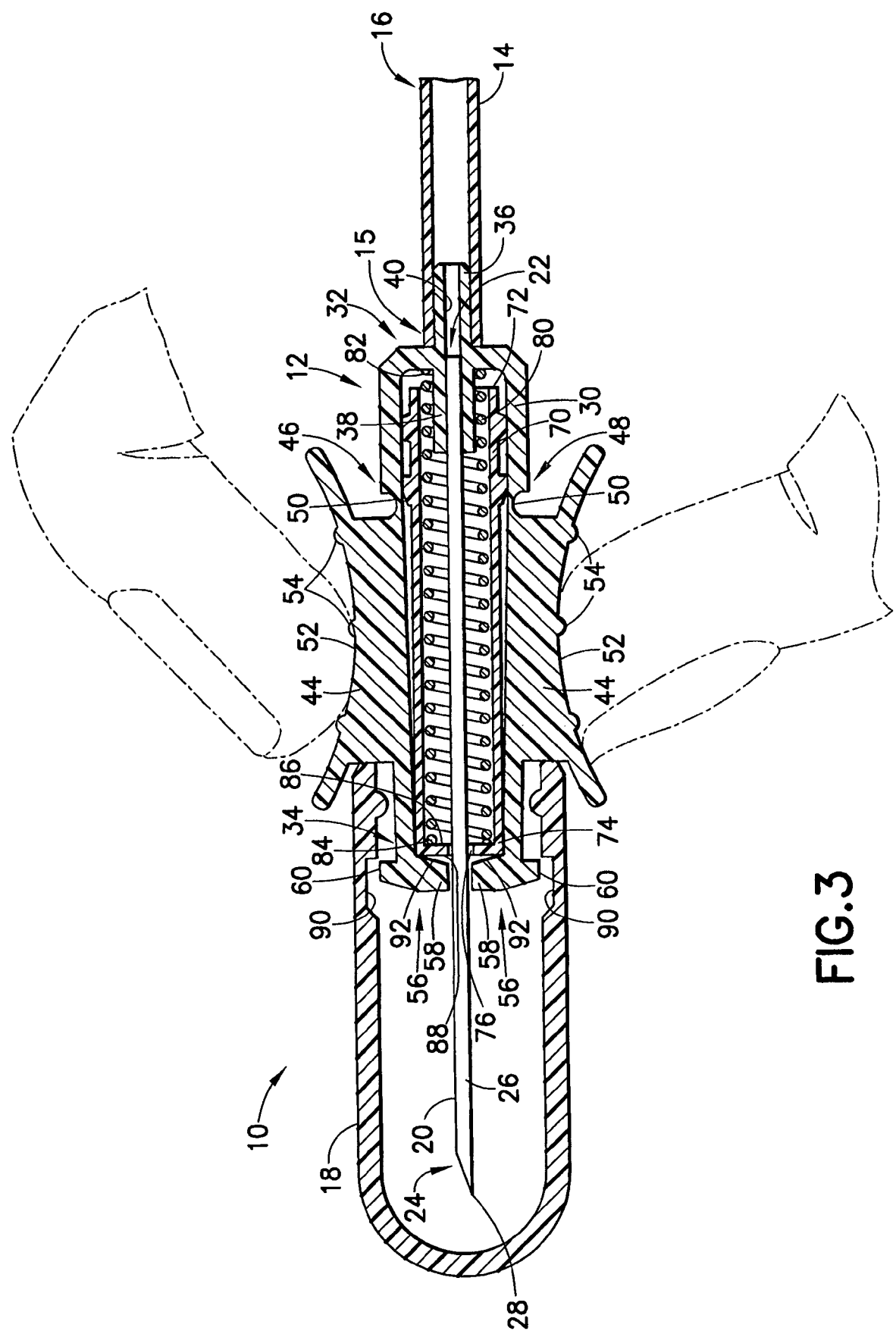
FIG. 3 is a longitudinal cross-sectional view of the blood collection set of FIG. 1, showing a user manipulating a shielding needle assembly portion of the blood collection set.

Referring to the drawings in which like reference characters refer to like parts throughout the several views thereof, FIG. 1 illustrates generally a blood collection set 10 in accordance with the present invention and its related features. The present invention is generally described in terms of a blood collection set, and encompasses such a blood collection set, as well as a shielding needle assembly for use in such a blood collection set.

As shown generally in FIG. 1, the blood collection set 10 includes a shielding needle device or assembly 12, a flexible tube 14 extending from the needle device or assembly 12 and having first and second ends 15, 16, and a packaging cover or shield 18 removably mounted to the needle assembly 12 opposite tube 14, such as through a frictional engagement. The blood collection set 10 and shielding needle assembly 12 of the present invention are shown in greater detail in FIGS. 2–8, and generally include a needle cannula 20, a hub 30, a needle cannula safety shield 70, and a drive member 80 for moving the safety shield 70.

The needle cannula 20 includes a proximal end 22 and an opposing distal end 24, with a lumen 26 extending through needle cannula 20 from the proximal end 22 to the distal end 24. The distal end 24 of needle cannula 20 is beveled to define a sharp puncture tip 28, such as an intravenous puncture tip. The puncture tip 28 is provided for insertion into a patient's blood vessel, such as a vein, and is therefore designed to provide ease of insertion and minimal discomfort during venipuncture.

The needle assembly 12 further includes the hub 30. The hub 30 may be a unitary structure, desirably molded from a thermoplastic material, or a multi-component structure as described herein. The hub 30 includes a proximal end 32 and a distal end 34. The proximal end 32 of the hub 30 includes an external portion or structure 36 for mating with the first end 15 of the flexible tube 14, and an internal portion or structure 38 for engaging the drive member 80, which is preferably in the form of a coil spring or like element for biasing the safety shield 70 in the manner described herein. The external and internal portions or structures 36, 38 are generally tubular shaped components adapted to cooperate with the flexible tube 14 and drive member 80, respectively. The external structure 36 may be adapted to cooperate with the flexible tube 14 in a friction-fit manner, and a suitable medical grade adhesive may be used to secure the connection.

As depicted in the Figures, the needle cannula 20 and the hub 30 are preferably separate parts that are preferably fixedly attached and secured through an appropriate medical grade adhesive, for example, epoxy and the like. In particular, the proximal end 22 of the needle cannula 20 is supported by the proximal end 32 of the hub 30 and, in particular, the internal structure 38 formed in the proximal end 32 of the hub 30. For this purpose, the hub 30 defines an opening 40 extending between the internal structure 38 and the external structure 36 for receiving and securing the proximal end 22 of the needle cannula 20 therein. The opening 40 preferably extends through the proximal end 32 of the hub 30 and is used to place the needle assembly 12 in fluid communication with the flexible tube 14, or another medical device, such as a tube holder, and like devices. The proximal end 22 of the needle cannula 20 may extend into the opening 40 and extend into the external structure 36 provided on the proximal end 32 of the hub 30. The needle cannula 20 is secured within the opening 40 by an appropriate medical grade adhesive, and generally extends toward the distal end of the needle assembly 12.

The hub 30 is generally tubular or cylindrical in shape, and preferably further includes two opposing release members 44. The release members 44 generally extend along opposing sides 46, 48 of the hub 30 and form part of the body of the hub 30. The release members 44 are generally adapted to maintain the safety shield 70 and drive member 80 in a pre-actuated state or position within the body of the hub 30, and also operate to release or actuate the drive member 80, which is generally operable to move the safety shield 70 to a shielding position relative to the needle cannula 20, as discussed in detail herein.

The release members 44 are desirably pivotally connected to the hub 30, for example by respective hinge structures 50 (i.e., hinges). The release members 44 are preferably integrally-molded with the body of the hub 30, which is preferably formed of molded plastic material. The hinge structures 50 are thus formed integrally (i.e., as a living hinge) with the release members 44 and the body of the hub 30. The hinge structures 50 permit the release members 44 to pivot relative to the body of the hub 30 and, in particular, to pivot inward toward a central longitudinal axis L of the blood collection set 10 and shielding needle assembly 12. The release members 44 may be formed separately from the hub 30 and connected thereto by conventional hinges. The release members 44 produce an angle vertex opening towards the distal end 34 of the hub 30. The release members 44 partially form the sidewall of the hub 30, but may pivotally extend inward into the hub 30.

The opposing release members 44 further include respective finger tabs 52 which provide locations for a user's fingers when manipulating the blood collection set 10 and needle assembly 12. The finger tabs 52 may include raised structures or protrusions 54, such as bumps, for improving the handling characteristics of the needle assembly 12 when manipulated by the user. The release members 44 each include distal ends 56 formed with opposing locking tabs 58, 60. The locking tabs 58, 60 are generally formed as inward-projecting locking tabs 58 and outward-projecting locking tabs 60, which are also referred to herein as first and second locking tabs 58, 60. The first or inward-projecting locking tabs 58 on the release members 44 are generally adapted to engage the safety shield 70, and the second or outward-projecting locking tabs 60 are generally adapted to engage the packaging shield or cover 18, as discussed further herein.

The needle assembly 12 further includes the safety shield 70, which extends generally coaxially about needle cannula 20 and is movable along needle cannula 20 between a first or retracted position coaxially received within the hub 30 (See FIGS. 2–5), and a second or extended position (See FIGS. 6 and 7) generally encompassing the needle cannula 20 and, more particularly, the puncture tip 28, as will be described in more detail herein. The safety shield 70 is a unitary structure, desirably molded from a thermoplastic material, and includes a proximal end 72 and a distal end 74. The distal end 74 defines a central opening 76 through which the needle cannula 20 extends. The central opening 76 permits the safety shield 70 to move along the needle cannula 20 between the retracted and extended positions. The safety shield 70 is further formed to encompass the drive member 80, as shown in FIGS. 2–5, prior to actuating the drive member 80, which is generally adapted to move the safety shield 70 axially along the needle cannula 20 from the retracted position to the extended position, as will be described in more detail herein.

The drive member 80 is generally coaxially positioned within the safety shield 70 and the hub 30 in the retracted position of the safety shield 70. The drive member 80 may be in the form of a coil compression spring or like biasing element and is generally adapted to move the safety shield 70 from the retracted position to the extended position. The drive member 80 has a proximal end 82 and a distal end 84. The proximal end 82 is generally disposed on the internal structure 38 formed internally at the proximal end 32 of the hub 30. The distal end 84 is generally in contact with the distal end 74 of the safety shield 70 and, in particular, an internal side 86 of the distal end 74 of the safety shield 70. The engagement of the distal end 84 of the drive member 80 with the distal end 74 of the safety shield 70 forms the physical interface between the drive member 80 and the safety shield 70 for moving the safety shield 70 from the retracted position to the extended position. The distal end 74 of the safety shield 70 further includes an outward-facing or distal end surface 88, which engages the first or inward-projection locking tabs 58 in the retracted position of the safety shield 70.

The packaging shield 18 is provided on the distal end 34 of the hub 30 and is preferably provided on the hub 30 during the manufacturing process of the blood collection set 10 and needle assembly 12. The packaging shield 18 is preferably in frictional engagement with the distal end 34 of the hub 30, but is secured in engagement with the hub 30 by a connecting structure described herein.

Alternatively, the release members 44 may represent the sidewalls of the hub 30, while they are radially flexible inwardly due to the physical structure of the hub 30. For example, the release members 44 (i.e., hub sidewalls) may be constructed to flex radially inwardly when lateral pressure is applied to opposing sides of the hub 30. To facilitate this flexing, the opposing sidewalls of the hub 30 may be constructed or molded with a thinner thickness than the proximal or distal portions of the hub 30, allowing for flexing of the opposing sides of the hub 30 at the release members 44. Such inward radial pressure at the release members 44 creates a compressive force establishing a frictional engagement against the safety shield 70 to hold the safety shield 70 in the retracted position. Such an arrangement may also include the locking tabs 58, 60 for further retention of the safety shield 70.

Figure 4:
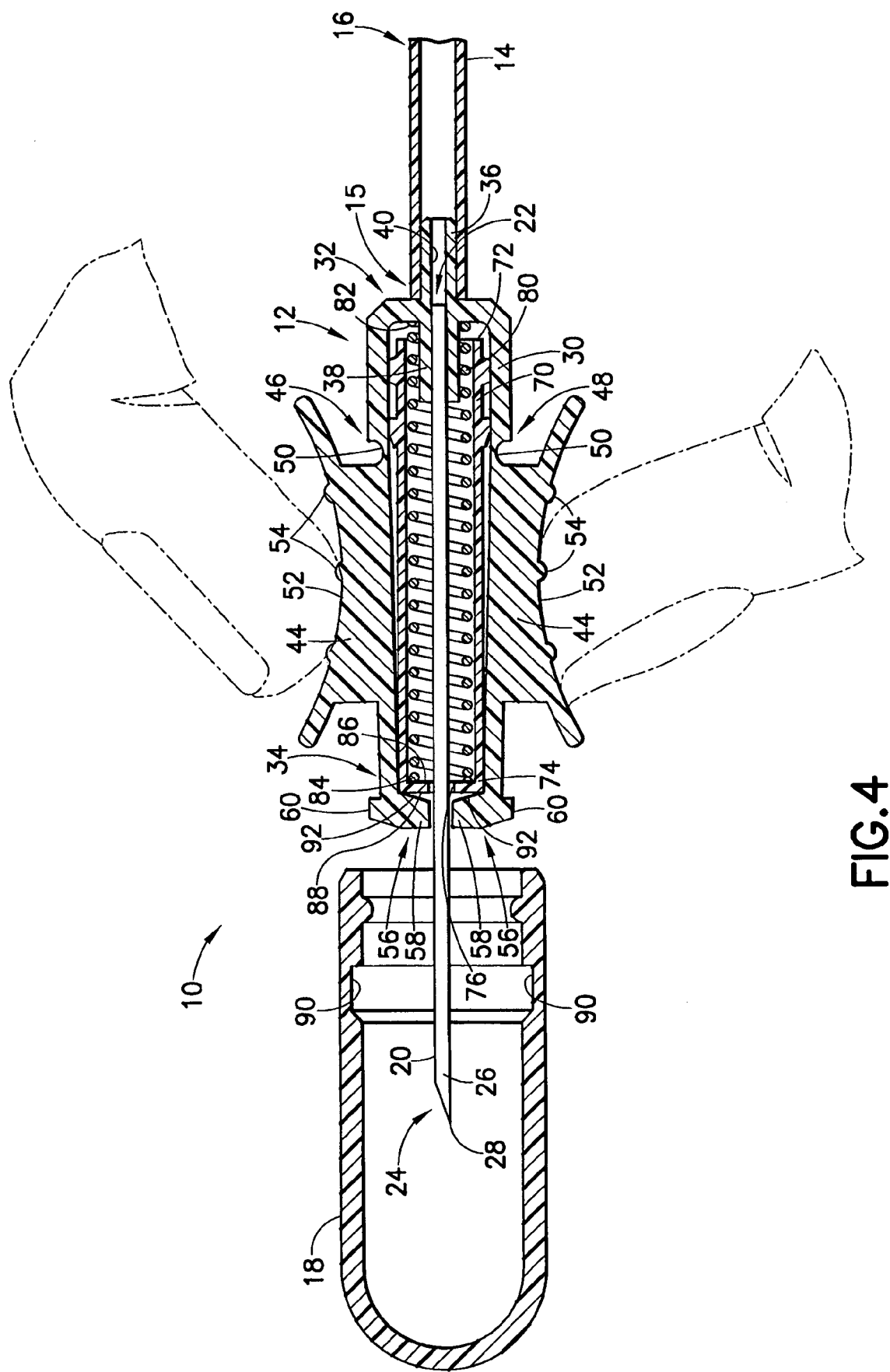
FIG. 4 is a longitudinal cross-sectional view of the blood collection set of FIG. 1, showing the user applying radial pressure to the shielding needle assembly portion of the blood collection set and the subsequent removal of the packaging shield.

The packaging shield 18 is generally adapted to maintain the needle assembly 12 in the pre-actuated state or condition shown, for example, in FIGS. 2–4, with the safety shield 70 in the retracted position. For this purpose, the packaging shield 18 is formed with an internal locking groove 90, which is engaged by the second or outward-projecting locking tabs 60 formed at the distal ends 56 of the release members 44. The engagement of the outward-projecting locking tabs 60 secures the packaging shield 18 on the distal end 34 of the hub 30, with the aid of the drive member 80, until the needle assembly 12 is actuated by a user.

In the pre-actuated or "pre-packaged" state or condition of the needle assembly 12, the drive member 80 exerts a distally-directed force on the internal side 86 of the safety shield 70, which urges the distal end 74 of the safety shield 70 into engagement or contact with the first or inward-projecting locking tabs 58 formed on the distal ends 56 of the release members 44. In particular, the distal end surface 88 of the safety shield 70 is urged into contact or engagement with the first or inward-projecting locking tabs 58 on the distal ends 56 of the release members 44. Without the presence of the packaging shield 18, the distally-directed force acting on the distal ends 56 of the release members 44 would cause the release members 44 to pivot outward about their respective hinge structures 50. However, this distally-directed force is prevented from prematurely actuating the needle assembly 12 by the presence of the packaging shield 18, which provides a counter-acting radial force maintaining the compression of the drive member 80 within the safety shield 70 and hub 30. The engagement of the first or outward-projecting locking tabs 60 with the locking groove 90 in the packaging shield 18 prevents premature removal of the packaging shield 18 from the distal end 34 of the hub 30, and therefore premature actuation of the needle assembly 12.

An optional mechanism for retaining the packaging shield 18 onto hub 30 includes using the locking tabs 60 as external threads to ride within corresponding internal threads (not shown) in the packaging shield 18. In this embodiment, the internal threads would act more like slots than true threads, and the packaging shield 18 would have to be rotated to a position where the locking tabs 60 (i.e., external threads) would allow for the packaging shield 18 to be removed from the hub 30. An alternative configuration to the foregoing could include the locking tabs 60 engaging internal circumferential slots in the packaging shield 18 which connect to internal axial slots in the packaging shield 18. In such a variation, rotation of the packaging shield 18 would cause the locking tabs 60 to slide within the circumferential slots until reaching the axial slots, which would allow the packaging shield 18 to be removed from the hub 30.

The blood collection set 10 may be packaged in a conventional blister package (not shown). Prior to use, the blood collection set 10 is removed from its package, and the second end 16 of the flexible tube 14 may be connected to an appropriate receptacle for providing fluid communication with the lumen 28 through the needle cannula 20. In use, the blood collection set 10 is provided with the needle assembly 12 and flexible tube 14 extending from needle assembly 12 and connected to an appropriate fixture (not shown), such as a blood collection receptacle.

Figure 5:
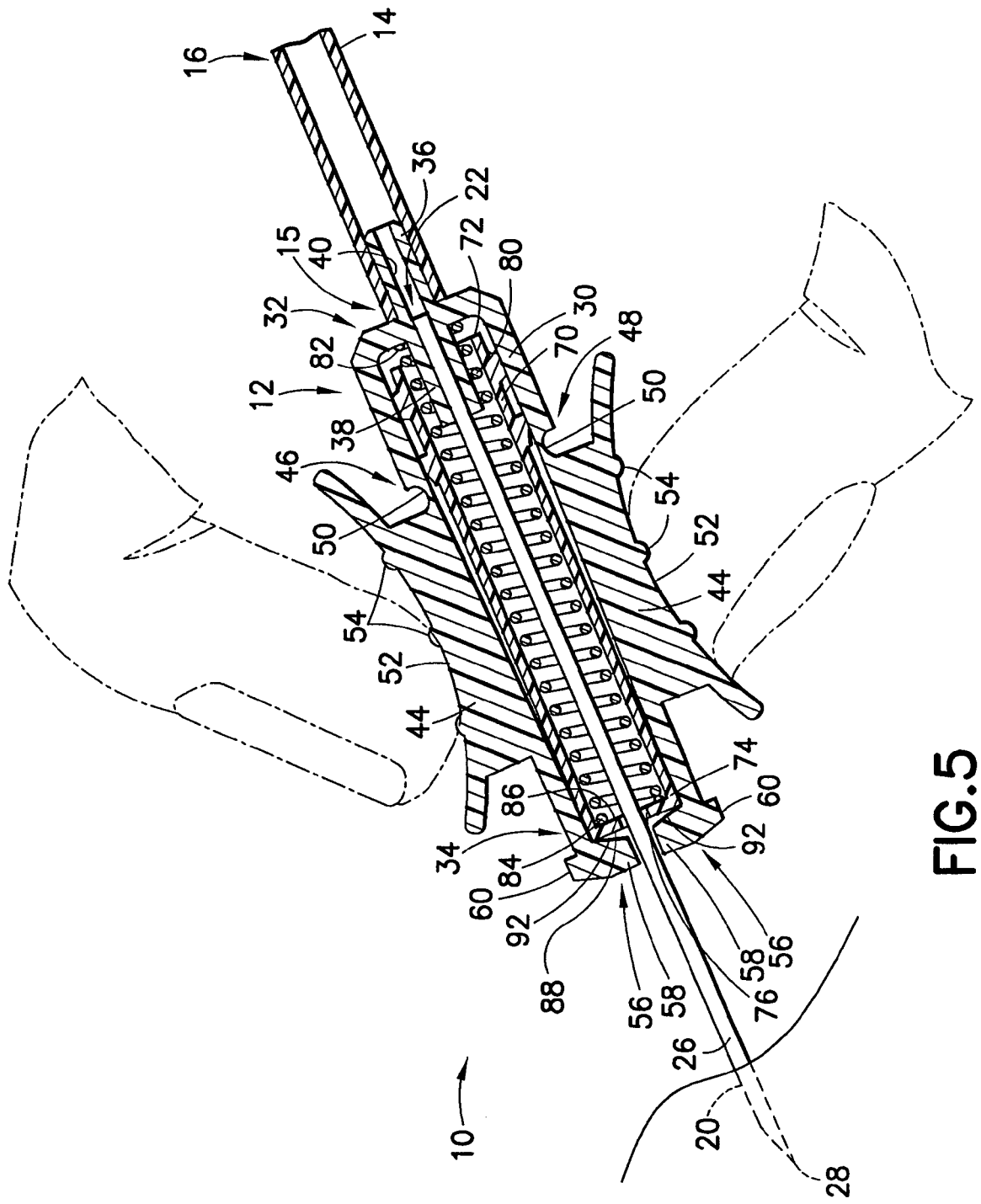
FIG. 5 is a cross-sectional view of the blood collection set of FIG. 1, showing a needle cannula of the blood collection set inserted into the body of a patient.

To use the blood collection set 10 and needle assembly 12, the user generally grasps the opposing finger tabs 52 provided on the needle assembly 12, as shown in FIGS. 3–5. The user then applies radial pressure to the finger tabs 52. FIG. 8 illustrates the direction of radially applied pressure that is necessary to begin actuation of the blood collection set 10 and needle assembly 12. As the user applies radial pressure to the finger tabs 52, the release members 44 will generally pivot inward toward the central longitudinal axis L of the blood collection set 10 and needle assembly 12. The release members 44 will generally pivot about their respective hinge structures 50, and will displace inward toward the central longitudinal axis L of the blood collection set 10 and needle assembly 12, as shown in FIG. 4. As shown in FIG. 4, the radial inward displacement of the release members 44 causes the second or outward-projection locking tabs 60 formed at the distal end 56 of the release members 44 to disengage substantially automatically from the locking groove 90 in the packaging shield 18. With the disengagement of the locking tabs 60 from the locking groove 90, the packaging shield 18 is released of secured engagement with the hub 30, and may be removed from the distal end 34 of the hub 30 by the user. The inward movement of the release members 44 generally reduces the diameter (i.e., cross sectional area) of the distal end 34 of the hub 30 and automatically releases the packaging shield 18 from the distal end 34.

The user preferably maintains the radial force applied to the finger tabs 52, which causes the release members 44 to remain in substantially laterally-extending positions along the lateral sides 46, 48 of the hub 30. In this configuration, the first or inward-projection locking tabs 58 remain engaged with the outward-facing or distal end surface 88 at the distal end 74 of the safety shield 70, and prevents the drive member 80 from moving the safety shield 70 from the retracted position to the extended position. In particular, the distal end surface 88 of the safety shield 70 engages opposing inward-facing surfaces 92 on the first or inward-projection locking tabs 58 formed on the release members 44. The radial pressure applied by the user maintains the engagement of the locking tabs 58 with the distal end 74 of the safety shield 70, thereby maintaining the safety shield 70 in the retracted position and counteracting the distally-directed biasing force of the drive member 80. The radial pressure applied to the finger tabs 52 generally takes the place of the removed packaging shield 18 for maintaining the safety shield 70 in the retracted position and counteracting the biasing force of the drive member 80.

The user may then urge the puncture tip 28 at distal end 24 of the needle cannula 20 into a targeted blood vessel of a patient in order to conduct a blood collection procedure or other procedure as desired. When the user releases the radial pressure applied to the finger tabs 52, the drive member 80 is free to exert a distally-directed biasing force on the distal end 74 of the safety shield 70. In particular, with the release of the radial pressure, the drive member 80 urges the outward-facing or distal end surface 88 of the safety shield 70 to slide along the inward-facing surfaces 92 on the inward-projecting locking tabs 58, and generally urges the release members 44 to spread radially apart. The inward-facing surfaces 92 of the locking tabs 58 may be tapered to facilitate the sliding movement of the distal end surface 88 of the safety shield 70, and the concurrent outward-directed movement of the release members 44. As used in this disclosure, the term "release of radial pressure" and like phrases used to describe how the user causes the needle assembly 12 to actuate the safety shield 70 is not intended to be limited to the complete discontinuing of radial pressure on the finger tabs 52. This terminology is specifically intended to include such a complete discontinuing of radial pressure, such as the user totally removing his or her fingers from the finger tabs 52, as well as a partial or sequential lessening or reducing of radial pressure on the finger tabs 52 sufficient to allow the drive member 80 to move the locking tabs 58 out of engagement with the distal end 74 of the safety shield 70 and move the safety shield 70 to the extended or shielding position. The biasing force inherent in the drive member 80 will determine the amount of lessening of the radial pressure required to allow the needle assembly 12 to actuate.

Figure 6:
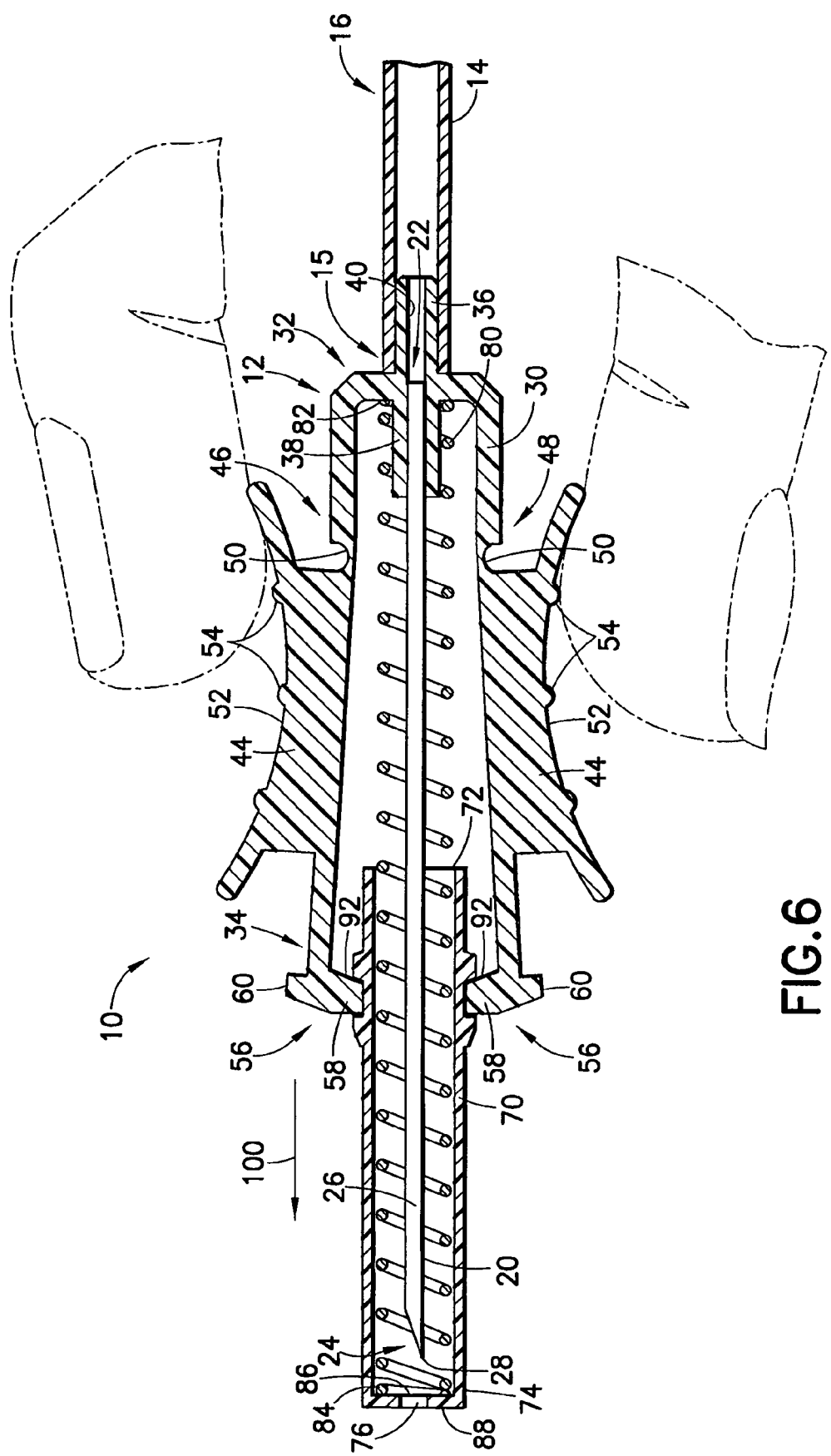
FIG. 6 is a longitudinal cross-sectional view of the blood collection set of FIG. 1, showing the blood collection set after the user has substantially released the radial pressure allowing the shielding needle assembly to shield a needle cannula of the assembly.
Figure 7:
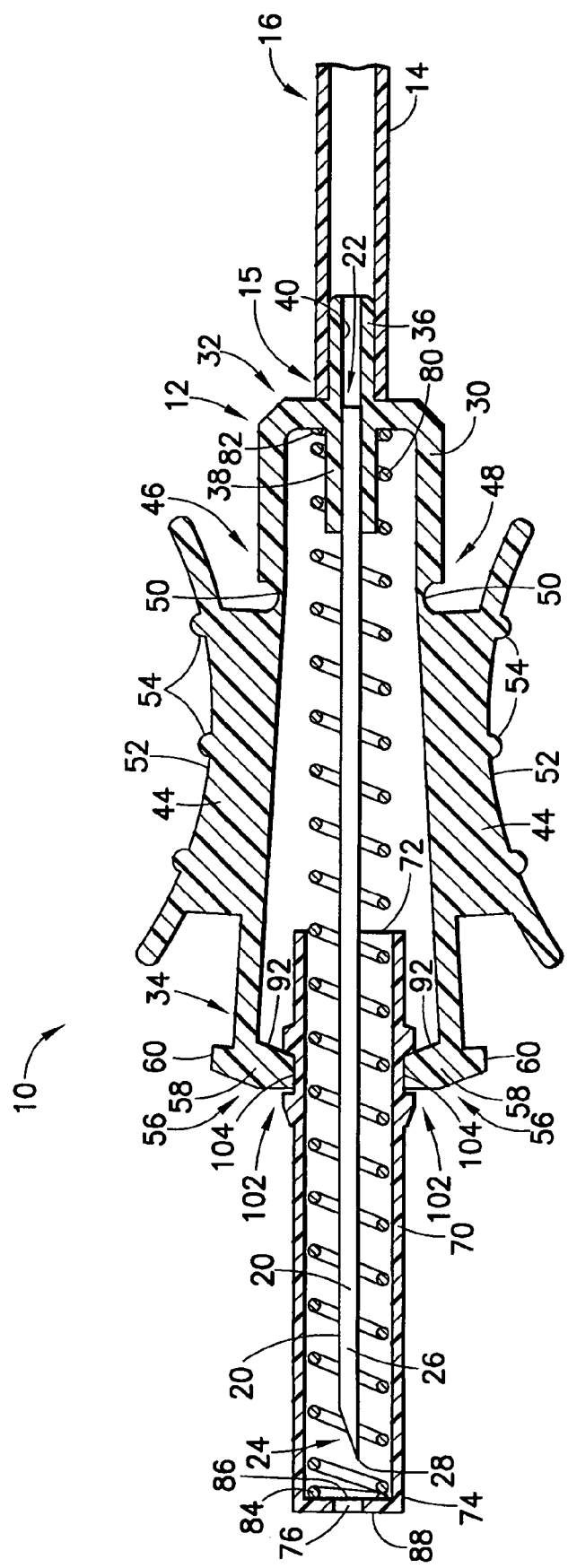
FIG. 7 is a longitudinal cross-sectional view of the blood collection set of FIG. 1, showing the final disposition of the shielding needle assembly shielding the needle cannula.

Once the locking tabs 58 are displaced radially out of engagement with the distal end 74 of the safety shield 70, the safety shield 70 is completely unrestrained and subject entirely to the distally-directed biasing force of the drive member 80. The drive member 80 propels the safety shield 70 distally along needle cannula 20 in an axial direction of arrow 100 (see FIG. 6), with the safety shield 70 sliding or gliding along needle cannula 20 toward distal end 24. During an actual blood collection procedure, the distal movement of the safety shield 70 will terminate when the distal end 74 of the safety shield 70 contacts the skin of the patient. The drive member 80 still exerts a distally-directed biasing force on the safety shield 70, but this force is resolved by the frictional force that acts on the needle cannula 20, as a result of being in the blood vessel of the patient. The user may then proceed to complete the blood collection procedure, for example using evacuated blood collection tubes or a syringe. The user then proceeds to remove the blood collection set 10 from the blood vessel of the patient using the finger tabs 52. As the needle cannula 20 is removed from the blood vessel of the patient, the safety shield 70 is urged by the drive member 80 to move closer to the distal end 24 of the needle cannula 20. As the needle cannula 20 is fully removed from the patient's blood vessel, the safety shield 70 is urged by the drive member 80 to fully encompass the needle cannula 20, as generally depicted in FIGS. 6 and 7. The drive member 80 now extends internally between the distal end 74 of the safety shield 70 and the internal structure 38 formed within the hub 30 at the proximal end 32 of the hub 30, and exerts a biasing force that will aid in preventing the re-emergence of the puncture tip 28 from the central opening 76 in the distal end 74 of the safety shield 70.

The safety shield 70 further includes an external locking structure 102 for securing the safety shield 70 in the extended position, once the needle assembly 12 has been actuated. The external locking structure 102 forms an external locking recess or groove 104, which is configured to be engaged by the inward-projecting locking tabs 58 when the safety shield 70 is moved to the extended position. In particular, when the safety shield 70 is moved to the extended position by the drive member 80, the locking tabs 58 preferably snap into engagement with the locking recess 104. It will be appreciated that the external locking recess 104 need not be continuous about the circumference of the safety shield 70. Likewise, the internal locking groove 90 in the packaging shield 18 need not be continuous around the internal circumference of the packaging shield 18. Moreover, it will further be appreciated that the needle shield 12 may be configured to operate with a single release member 44 rather than the opposing pair of release members 44 discussed previously. However, the use of two opposing release members 44 is believed to be more intuitive for the user of the blood collection set 10 and needle assembly 12, and is presently preferred.

The shielding feature of the present invention is passively actuated upon normal usage of the device. In particular, upon removal of the packaging shield prior to insertion, the safety feature is primed and charged, ready for shielding the needle once the user releases the opposing finger tabs. Moreover, in some instances, the needle assembly may be dropped or knocked from the hand of the user before, during, or after use. The shielding feature described above will commence automatically when the needle assembly is dropped or knocked from the user's hand. Thus, the automatic shielding may be triggered by the intentional or unintentional release of the finger tabs by the user.

Additionally, a user, such as a medical practitioner, does not always enter the targeted blood vessel during the first venipuncture attempt. However, a medical practitioner typically retains a close grip on the needle assembly until the targeted blood vessel has been entered. In this instance, the continued gripping of the finger tabs will prevent the needle assembly from shielding until the targeted blood vessel has been punctured. The second attempt at accessing a targeted blood vessel generally is a very low risk procedure in which the user's hand is spaced considerably from the puncture tip of the needle cannula. Thus, the blood collection set, according to the present invention, does not involve the inconvenience of having to use a new blood collection set following each unsuccessful venipuncture attempt.

While the needle assembly of the present invention has been described in terms of one embodiment for use in connection with a blood collection system, it is further contemplated that the needle assembly could be used with other medical procedures, such as in conjunction with a conventional intravenous infusion set, which are well-known in the art for use with needle assemblies. While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

The invention claimed is:

1. A shielding needle assembly, comprising:
a needle cannula having a proximal end and a distal end with a puncture tip;
a hub supporting the needle cannula, the hub including at least one release member;
a safety shield movably associated with the hub from a retracted position disposed generally coaxially within the hub to an extended position shielding the puncture tip of the needle cannula; and
a drive member associated with the hub and adapted to move the safety shield from the retracted to the extended positions, wherein application of radial pressure to the at least one release member causes the at least one release member to engage the safety shield and maintain the safety shield in the retracted position, and wherein at least partial release of the radial pressure allows the drive member to disengage the at least one release member from the safety shield and move the safety shield from the retracted position to the extended position.

2. A shielding needle assembly as in claim 1, wherein the drive member comprises a coil spring.

3. A shielding needle assembly as in claim 1, wherein the at least one release member is pivotally connected to the hub substantially at a proximal end of the hub.

4. A shielding needle assembly as in claim 3, further including a finger tab provided on the at least one release member for applying the radial pressure.

5. A shielding needle assembly as in claim 1, wherein the at least one release member includes a pair of opposing release members pivotally connected to the hub substantially at a proximal end of the hub.

6. A shielding needle assembly as in claim 5, further including a finger tab provided on each of the release members for applying the radial pressure to the release members.

7. A shielding needle assembly as in claim 1, wherein the at least one release member includes a locking tab adapted to engage a locking recess in the safety shield in the extended position of the safety shield.

8. A shielding needle assembly as in claim 7, wherein the locking recess extends circumferentially about the safety shield.

9. A shielding needle assembly as in claim 1, further including a packaging shield disposed on a distal end of the hub and enclosing the puncture tip of the needle cannula in the retracted position of the safety shield.

10. A shielding needle assembly as in claim 9, wherein the at least one release member is pivotally connected to the hub, and includes a locking tab engaging a locking groove in the packaging shield preventing removal of the packaging shield until the application of the radial pressure to the at least one release member causes the at least one release member to pivot radially inward and disengage the locking tab from the locking groove.

11. A needle assembly as in claim 1, wherein the hub is capable of direct or indirect fluid communication with a syringe.

12. A needle assembly as in claim 1, wherein the hub is capable of direct or indirect fluid communication with a blood collection tube holder.

13. A shielding blood collection set, comprising:
a flexible tube having opposed first and second ends, the first end of the tube adapted for connection to a receptacle;
a needle cannula having a proximal end and a distal end with a puncture tip;
a hub having a proximal end and a distal end, an interior portion of the hub proximal end supporting the needle cannula proximal end and the second end of the tube connected to an exterior portion of the hub proximal end, the hub including at least one release member;
a safety shield movably associated with the hub from a retracted position disposed generally coaxially within the hub to an extended position shielding the puncture tip of the needle cannula; and
a drive member associated with the hub and adapted to move the safety shield from the retracted to the extended positions, wherein application of radial pressure to the at least one release member causes the at least one release member to engage the safety shield and maintain the safety shield in the retracted position, and wherein at least partial release of the radial pressure allows the drive member to disengage the at least one release member from the safety shield and move the safety shield from the retracted position to the extended position.

14. A shielding blood collection set as in claim 13, wherein the drive member comprises a coil spring.

15. A shielding blood collection set as in claim 13, wherein the at least one release member is pivotally connected to the hub substantially at the hub proximal end.

16. A shielding blood collection set as in claim 15, further including a finger tab provided on the at least one release member for applying the radial pressure.

17. A shielding blood collection set as in claim 13, wherein the at least one release member includes a pair of opposing release members pivotally connected to the hub substantially at the hub proximal end.

18. A shielding blood collection set as in claim 17, further including a finger tab provided on each of the release members for applying the radial pressure to the release members.

19. A shielding blood collection set as in claim 13, wherein the at least one release member includes a locking tab adapted to engage a locking recess in the safety shield in the extended position of the safety shield.

20. A shielding blood collection set as in claim 19, wherein the locking recess extends circumferentially about the safety shield.

21. A shielding blood collection set as in claim 13, further including a packaging shield disposed on the hub distal end and enclosing the puncture tip of the needle cannula in the retracted position of the safety shield.

22. A shielding blood collection set as in claim 21, wherein the at least one release member is pivotally connected to the hub, and includes a locking tab engaging a locking groove in the packaging shield preventing removal of the packaging shield until the application of the radial pressure on the at least one release member causes the at least one release member to pivot radially inward and disengage the locking tab from the locking groove.

23. A shielding needle assembly, comprising:
a needle cannula having a proximal end and a distal end with a puncture tip;
a hub supporting the needle cannula, the hub including at least one release member;
a safety shield movably associated with the hub from a retracted position disposed generally coaxially with the hub to an extended position shielding the puncture tip of the needle cannula;
a drive member associated with the hub and adapted to move the safety shield from the retracted position to the extended position; and
a packaging shield disposed on a distal end of the hub and enclosing the puncture tip of the needle cannula in the retracted position of the safety shield, wherein the at least one release member is pivotally connected to the hub, and includes a locking tab engaging a locking groove in the packaging shield preventing removal of the packaging shield, and wherein application of radial pressure to the at least one release member causes the at least one release member to pivot radially inward and disengage the locking tab from the locking groove, thereby substantially releasing the packaging shield from the hub, and farther causes the at least one release member to engage the safety shield and maintain the safety shield in the retracted position, and wherein at least partial release of the radial pressure allows the drive member to disengage the at least one release member from the safety shield and move the safety shield from the retracted position to the extended position.

24. A shielding needle assembly as in claim 23, wherein the drive member comprises a coil spring.

25. A shielding needle assembly as in claim 23, wherein the at least one release member is pivotally connected to the hub substantially at a proximal end of the hub.

26. A shielding needle assembly as in claim 25, further including a finger tab provided on the at least one release member for applying the radial pressure.

27. A shielding needle assembly as in claim 23, wherein the at least one release member includes a pair of opposing release members pivotally connected to the hub substantially at a proximal end of the hub.

28. A shielding needle assembly as in claim 27, further including a finger tab provided on each of the release members for applying the radial pressure to the release members.

29. A shielding needle assembly as in claim 23, wherein the at least one release member includes a second locking tab adapted to engage a locking recess in the safety shield in the extended position of the safety shield.

30. A shielding needle assembly as in claim 29, wherein the locking recess in the safety shield extends circumferentially about the safety shield.

31. A shielding needle assembly, comprising:
- a needle cannula having a proximal end and a distal end with a puncture tip;
- a hub supporting the needle cannula, the hub including at least one release member;
- a safety shield movably associated with the hub from a retracted position disposed generally coaxially within the hub to an extended position shielding the puncture tip of the needle cannula;
- a packaging shield removably engageable with the hub, the packaging shield covering the needle cannula proximal end; and
- a drive member associated with the hub and adapted to move the safety shield from the retracted to the extended positions, wherein application of radial pressure applied to the at least one release member is required for removal of the packaging shield from the hub, and sequential change in radial pressure applied to the at least one release member is required for allowing the drive member to disengage the at least one release member from the safety shield and move the safety shield from the retracted position to the extended position.

32. A shielding needle assembly as in claim 31, wherein the sequential change in radial pressure is a lessening of pressure.

* * * * *